United States Patent [19]

Cole

[11] 4,217,269
[45] Aug. 12, 1980

[54] DIPEPTIDE CHROMOGENIC SUBSTRATES

[75] Inventor: John W. Cole, Deerfield, Ill.

[73] Assignee: Abbott Laboratories, North Chicago, Ill.

[21] Appl. No.: 23,062

[22] Filed: Mar. 23, 1979

[51] Int. Cl.² .................. C07C 103/52; C07G 7/00
[52] U.S. Cl. .................. 260/112.5 R; 424/177
[58] Field of Search .................. 260/112.5 R

[56] References Cited

U.S. PATENT DOCUMENTS

| | | | |
|---|---|---|---|
| 3,884,896 | 5/1975 | Blomback et al. | 260/112.5 R |
| 4,016,042 | 4/1977 | Svendsen | 260/112.5 R |
| 4,061,625 | 12/1977 | Ekenstam et al. | 260/112.5 R |
| 4,070,245 | 1/1978 | Svendsen | 260/112.5 R |

Primary Examiner—Delbert R. Phillips
Assistant Examiner—Blondel Hazel
Attorney, Agent, or Firm—John J. McDonnell

[57] ABSTRACT

The present invention comprises compounds of the formula

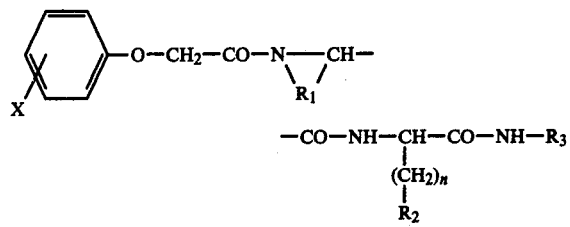

and the biologically acceptable acid addition salts thereof, wherein $R_1$ represents an alkylene having 2-4 carbon atoms; $R_2$ is selected from the group consisting of amino and quanyl; $R_3$ is selected from the group consisting of nitrophenyl, methylnitrophenyl, dinitrophenyl, naphthyl and nitronaphthyl; X represents halo or lower alkyl having 1-4 carbon atoms; and n is 3 or 4. The compounds of the present invention are analytical reagents useful for measuring proteolytic enzymes such as thrombin and trypsin. The enzymatic hydrolysis of the invention compounds provides a chromogenic amine by which the proteolytic enzyme concentration can be determined spectrophotometrically.

7 Claims, No Drawings

DIPEPTIDE CHROMOGENIC SUBSTRATES

BACKGROUND OF THE INVENTION

The present invention relates to reagents which are useful in the quantitative determination of proteolytic enzymes. More particularly, the invention relates to peptide derivatives which are substrates for enzymes of the class E.C.3.4.4. These enzymes cleave amide linkages in peptide chains on the carboxyl side of arginine and lysine residues.

Classical substrates for trypsin, thrombin, and related enzymes are amides such as α-N-benzoyl-DL-arginyl-p-nitroanilide, L-lysyl-p-nitroanilide, α-N-benzoyl-DL-arginyl-2-naphthylamide and other di, tri and higher order arginine and lysine peptides with chromogenic amide leaving groups [B. F. Erlanger, et al., *Arch. Bioch. Biop.*, 95 (1961)271; A. Riedel and E. Wunsch, *Z. Physiol. Chem.*, 316 (1961)1959; R. E. Plapinger, et al., *J. Org. Chem.*, 30 (1965)1781; L. Svendsen, et al., *Thrombosis Res.*, 1 (1972)267. U.S. Pat. No. 3,884,896]

U.S. Pat. No. 4,070,245 describes compounds of the structure:

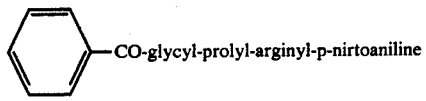
CO-glycyl-prolyl-arginyl-p-nirtoaniline

U.S. Pat. No. 4,061,625 describes compounds of the structure:

Phenylalanyl-prolyl-arginyl-p-nitroaniline

The above prior art compounds are p-nitroanilide derivatives of tripeptides terminating with glycine, phenylalanine or derivatives thereof. The present invention compounds differ from the prior art compounds in that the later are phenoxyacetyl derivatives of dipeptides. These structural differences are illustrated by comparing the structure of phenoxyacetyl-prolyl-arginyl-p-nitroaniline with the prior art compounds.

BRIEF DESCRIPTION OF THE INVENTION

The present invention comprises compounds of the formula

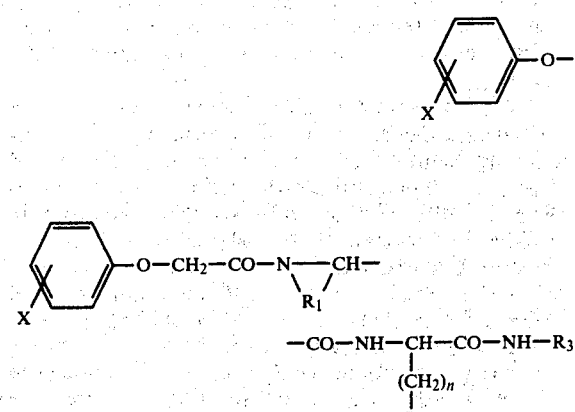

and the biologically acceptable acid addition salts thereof, wherein $R_1$ represents an alkylene having 2–4 carbon atoms; $R_2$ is selected from the group consisting of amino and quanyl; $R_3$ is selected from the group consisting of nitrophenyl, methylnitrophenyl, dinitrophenyl, naphthyl and nitronaphthyl; X represents halo or lower alkyl having 1–4 carbon atoms; and n is 3 or 4. The compounds of the present invention are analytical reagents useful for measuring proteolytic enzymes such as thrombin and trypsin. The enzymatic hydrolysis of the invention compounds provides a chromogenic amine by which the proteolytic enzyme concentration can be determined spectrophotometrically.

DETAILED DESCRIPTION OF THE INVENTION

The present invention encompasses compounds represented by the formula

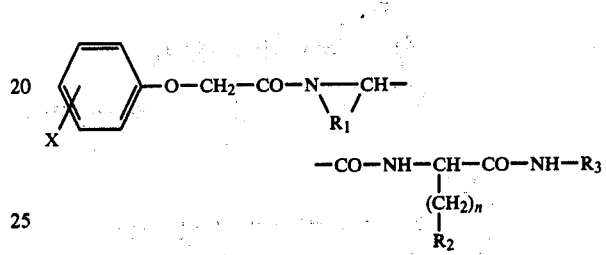

and the biologically acceptable acid addition salts thereof. X represents halo such as fluoro, chloro, bromo or lower alkyl having 1–4 carbon atoms such as methyl, ethyl, propyl, isopropyl, butyl, t-butyl. $R_1$ represents an alkylene having 2–4 carbon atoms belonging to an amino acid residue selected from the group consisting of L-proline (where $R_1$ is propylene), L-pipecolic acid (where $R_1$ is butylene, and L-azetidine carboxylic acid (where $R_1$ is ethylene). $R_2$ represents the amino or quanyl moiety belonging to an amino acid residue selected from the group consisting of L-arginine or L-ornithine (where n equals 3) or L-lysine (where n equals 4). $R_3$ is selected from the group consisting of nitrophenyl, methylnitrophenyl, dinitrophenyl, naphthyl and nitronaphthyl. $R_3$ is preferably nitrophenyl but other art recognized chromogenic substitutes for nitrophenyl may be used [Plapinger, Nachlas, Seligman and Seligman, *J. Organic Chemistry*, 30, (1965)1781, and U.S. Pat. No. 3,884,896].

Preferred compounds are represented by the formula

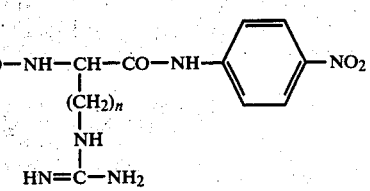

and the biologically acceptable acid addition salts thereof, wherein X, $R_1$, and n are as previously defined.

The most preferred compounds are represented by the formula

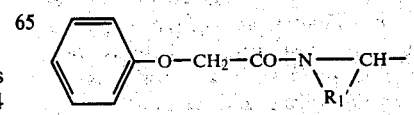

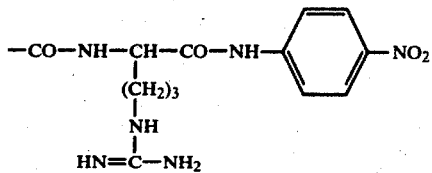

and the biologically acceptable acid addition salts thereof, wherein $R_1'$ represents an alkylene having 3 or 4 carbon atoms.

Compounds of the present invention are prepared by the following scheme:

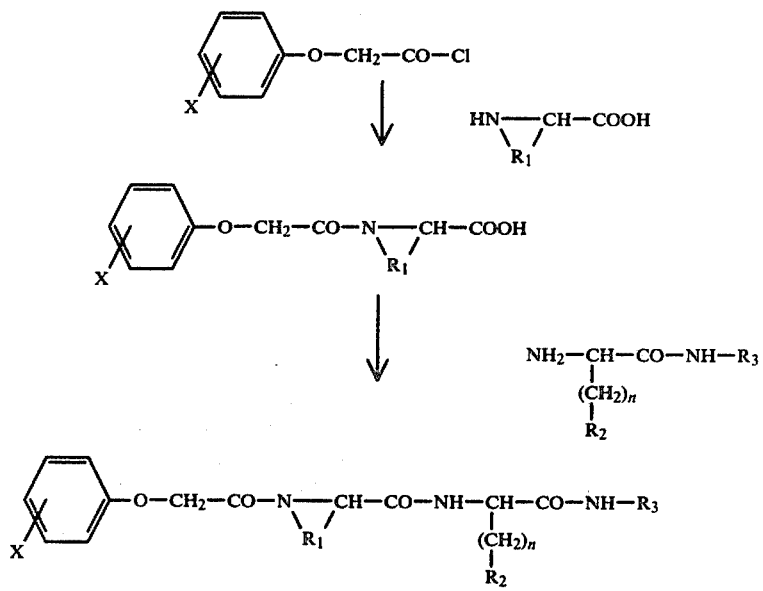

Typically, phenoxacetyl chloride is reacted with L-proline in anhydrous pyridine to provide phenoxyacetyl-L-proline. This product is coupled with arginyl-p-nitroanilide in anhydrous pyridine by conventional carbodiimide coupling techniques. In this manner, the following representative compounds of the present invention are prepared:

phenoxyacetyl-L-prolyl-L-arginyl-p-nitroanilide,
phenoxyacetyl-L-pipecolyl-L-arginyl-p-nitroanilide,
phenoxyacetyl azetidine carbonyl-L-arginyl-p-nitroanilide,
phenoxyacetyl-L-prolyl-L-lysyl-p-nitroanilide,
phenoxyacetyl-L-pipecolyl-L-lysyl-p-nitroanilide,
phenoxyacetyl-L-azetidine carbonyl-L-lysyl-p-nitroanilide,
phenoxyacetyl-L-prolyl-L-ornithyl-L-p-nitroanilide,
phenoxyacetyl-L-pipecolyl-L-ornithyl-p-nitroanilide,
phenoxyacetyl-L-azetidine carbonyl-L-ornithyl-p-nitroanilide,
and the biologically acceptable acid addition salts thereof.

The acid addition salts within the scope of the present invention compounds are of the biologically acceptable acid salts selected from mineral acids such as hydrochloric, hydrobromic, hydrosulfuric, and hydrophosphoric or from organic acids such as formic, acetic, oxalic, tartaric, methanesulfonic and benzenesulfonic. Those skilled in the art will recognize the equivalence of other organic and mineral acids.

Another procedure for preparing the present invention compounds involves a method of coupling phenoxyacetic acid to N-t-butoxycarbonyl-L-prolyl-$N^w$-(4-methoxybenzenesulfonyl)-L-arginyl-p-nitroanilide. This procedure provides phenoxyacetyl-L-prolyl-$N^2$-(4-methoxybenzenesulfonyl)-L-arginyl-p-nitroanilide which is converted to methanesulfonic salt of phenoxyacetyl-L-prolyl-L-arginyl-p-nitroanilide by an acid cleavage step. This methanesulfonic salt may be converted to acetate salt or other salt equivalents known in the art particularly by use of an ion exchange method [Encyclopedia of Chemistry, 3rd ed. "Ion Exchangers", Hampel and Hawley, ED., Reinhold Pub. Co. (1973) N.Y.].

In a typical procedure using the chromogenic substrates of the invention, the enzyme, such as trypsin or thrombin, and the substrate are mixed in a buffer solution and the reaction is followed spectrophotometrically. The concentration of substrate is varied, while the enzyme concentration is kept constant. As is well known in the art, a plot of the optical density as a function of time gives a curve from which the rate of reaction can be determined. Co-respondingly, a Lineweaver-Burk plot therefrom permits determination of $K_m$ and $K_{cat}$.

Table I presents Michaelis-Menten kinetic data and illustrates the usefulness of phenoxyacetyl-L-prolyl-L-arginyl-p-nitroanilide for determining thrombin and trypsin. The kinetic data was obtained from reactions run in 0.17M TRIS buffer or 0.1M potassium phosphate (with 0.1% gelatin) buffers at pH 7.4 and 7.0, respectively. The reaction mixture contained highly purified bovine trypsin at $1.21 \times 10^{-9}$M or highly purified human thrombin at $1.04 \times 10^{-9}$M and 50 μl of phenoxyacetyl-L-prolyl-L-arginyl-p-nitroanilide solution which has been obtained by diluting said solution nearly 1:400 with a solvent of 0.025M dimethyl formamide and ethanol in a 1:1 ratio. The reaction was analyzed on an Abbott ABA ®-100 bichromatic analyzer (sold by Abbott Laboratories, North Chicago, Il) at 406nm and 37° C.

TABLE I

| Buffer | Thrombin | | Trypsin | |
|---|---|---|---|---|
| | $K_{cat}$ Sec$^{-1}$ | $k_m$ ×10$^4$M | $K_{cat}$ Sec$^{-1}$ | $k_m$ ×10$^4$M |
| 0.17M TRIS | 168 | 6.4 | 178 | 4 |
| 0.1M Phosphate | 329 | 2.4 | 310 | 4.3 |

Clinically, the chromogenic substrates are used to measure antithrombin III.

Antithrombin III (AT-III) is the major component of the anticoagulation system. It inhibits a variety of serine proteases by forming a 1:1 complex via serine, the active center of such enzymes. The presence of heparin increases the rate of reactin of AT-III with such proteases approximately 100-fold, making AT-III the only plasma component involved in this rapid inhibition reaction.

The chemistry of the AT-III is described in the following equations:

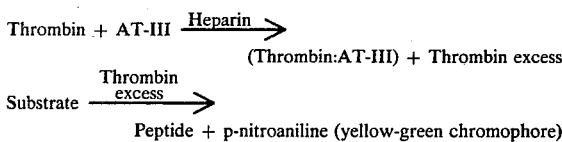

Since the presence of heparin potentiates the activity of AT-III, it is possible to delineate the inhibition due to AT-III from that of other plasma proteins which can also inhibit thrombin. Thus, one measures total AT-III activity as an entity distinct from the "progressive antithrombin activity" which is measured in the absence of heparin. As a result, one can clearly identify a defect in the anticoagulation system as one associated with AT-III rather than other protein inhibiting mechanisms.

This test relies on the fact that human AT-III in a specimen inhibits human α-thrombin in a 1:1 molar ratio. Excess thrombin is free to hydrolyse a colorless chromogenic substrate. When this substrate is cleaved, it releases, for example, in the absorbance spectrum shown by the development of a yellow-green color. This cleavage of the substrate is analogous to the cleavage of the arginyl-glycine bond in fibrinogen which results in the formation of fibrin. By monitoring the color development of the reaction mixture, one can follow the course of the turnover of substrate by thrombin. Since the amount of AT-III and the amount of color produced are inversely proportional, the level of AT-III can readily be determined.

The following examples illustrate the present invention and are not intended to limit the invention in scope or spirit.

EXAMPLE I 2.53 grams (g) of L-proline and 20 milliliters (ml) of anhydrous pyridine are mixed in a flask cooled by an ice bath, and 3.42 g of phenoxyacetyl chloride is added dropwise over about a 20-minute period. The mixture is warmed by water bath to room temperature, and the solvent evaporated under reduced pressure (in vacuo), leaving a viscous syrup. The syrup is dissolved in 15 ml water and the water is evaporated in vacuo. The residue is dissolved in 20 ml water, and the resulting solution is filtered, and subsequently treated with 10 ml of 2 N hydrochloride. The resulting precipitate, crude phenoxyacetyl-L-proline, is purified on a chromatographic column containing 80 g of silica gel. The column is eluted with a solvent mixture composed of equal volumes of isopropanol and toluene to provide phenoxyacetyl-L-proline.

EXAMPLE II

Following the procedure in Example I replacing L-proline with L-pipecolic acid provides phenoxyacetyl-L-pipecolic acid.

EXAMPLE III

Following the procedure in Example I replacing L-proline with L-azetidinecarboxylic acid provides phenoxyacetyl-L-azetidine carboxylic acid.

EXAMPLE IV 0.85 g of benzyloxycarbonyl-w-nitro-L-arginyl-p-nitroanilide is placed in a teflon reaction vessel and cooled with a dry-ice-acetone bath, 5 ml of liquid hydrogen fluoride is then added to the vessel and the temperature of the vessel is adjusted to 0° C. with an ice-water bath. The resulting mixture is stirred for one hour with a teflon-coated magnetic bar. Any excess hydrogen fluoride is removed by evapoation in vacuo. The residue is washed four times with 6 ml portions of anhydrous ether, flushed with nitrogen and then is dissolved in 8 ml of 10% aqueous acetic acid. The resulting solution is filtered through a column containing 10 g of basic resin acetate. The resin is rinsed with about a 10 % aqueous acetic acid solution. The solvent is removed from the filtrate by evaporation under reduced pressure and the residue is purified by passage through a chromatographic column containing 70 g of silica gel. The column is eluted with a solvent mixture composed of isopropanol-water-acetic acid in a ratio of 70:28:2. Fractions with the highest purity of L-arginyl-p-nitroanilide acetate are collected and the solvent evaporated in vacuo to provide L-arginine-p-nitroanilide acetate which is dissolved in 8 ml of 1 N hydrogen chloride. The solvent is evaporated and the residue redissolved in 8 ml of water. The solvent is again evaporated providing L-arginyl-p-nitroanilide dihydrochloride.

EXAMPLE V 0.30 g of L-arginyl-p-nitroanilide dihydrochloride, 0.22 g of phenoxyacetyl-L-proline and 3.5 ml of anhydrous pyridine is added to a flask cooled to 10° C. in a water bath, and stirred for five minutes. Then 0.25 g of dicyclohexylcarbodiimide is added, and the mixture stirred for approximately 20 hours at room temperature. 0.5 ml of water is added to destroy the excess diimide. After about two hours, 5 ml of water is added and the solvent evaporated in vacuo. The residue is extracted with two 10 ml portions of water at approximately 35° C., filtered, and the solvent evaporated in vacuo to yield a crude product. This product is further pruified on a chromatographic column containing 35 g of silica gel. The column is eluted with a solvent mixture of isopropanol-water-acetic acid in a ratio of 75:20:5. Fractions from the column provide phenoxyacetyl-L-prolyl-L-arginyl-p-nitroanilide hydrochloride.

EXAMPLE VI

In a round bottom flask suitable for vacuum, 0.35 g of N$^α$-t-butoxycarbonyl-N$^ε$-benzyloxycarbonyl-L-lysyl-p-nitroaniline (as described in U.S. Pat. No. 3,884,896) is treated with 4 ml of 4 M hydrogen chloride in anhydrous dioxane for one hour at room temperature, followed by evaporation of the solvent in vacuo to provide a residue. The residue is washed with anhydrous ether, and dried in vacuo. This product, $N^\epsilon$-benzyloxycarbonyl-lysyl-p-nitroanilide hydrochloride, is used in the coupling procedure of Example V in place of the L-arginyl-p-nitroanilide dihydrochloride, yielding phenoxylacetyl-L-prolyl-$N^\epsilon$-benzyloxycarbonyl-L-lysyl-p-nitroanilide which is then treated with 32% hydrogen bromide in acetic acid at room temperature for one hour, followed by evaporation of the solvent in vacuo and the addition of anhydrous ether to precipitate phenoxyacetyl-L-prolyl-L-lysyl-p-nitroanilide hydrobromide.

EXAMPLE VII

Following the procedure in Example VI, replacing $N^\alpha$-t-butoxycarbonyl-$N^\epsilon$-benzyloxycarbonyl-L-lysyl-p-nitroaniline with $N^\alpha$-t-butoxycarbonyl-$N^\Delta$-benzyloxycarbonyl-L-ornithyl-p-nitroaniline produces the product $N^\Delta$-benzyloxycarbonyl-L-ornithyl-p-nitroaniline-hydrogen chloride. This product is used in the coupling procedure of Example V in place of L-arginyl-p-nitroanilide dihydrochloride, yielding phenoxylacetyl-L-prolyl-$N^\Delta$-benzyloxycarbonyl-L-ornithyl-p-nitroaniline which is then treated with 32% hydrogen bromide as described in Example VI, providing phenoxyacetyl-L-prolyl-L-ornithyl-p-nitroanilide hydrobromide.

EXAMPLE VIII

Following the procedure in Example V, replacing 0.22 g of phenoxyacetyl-L-proline, with 0.23 g of phenoxyacetyl-L-pipecolic acid, provides upon purification, phenoxyacetyl-L-piepcolyl-L-arginyl-p-nitroanilide hydrochloride.

EXAMPLE IX

Following the procedure in Example V replacing L-arginyl-p-nitroanilide dihydrochloride with $N^\epsilon$-benzyloxycarbonyl-L-lysyl-p-nitroanilide hydrochloride and replacing phenoxyacetyl-L-proline with phenoxyacetyl-L-pipecolic acid provides upon purification phenoxyacetyl-L-piepcolyl-$N^\epsilon$-benzyloxy carbonyl-L-lysyl-p-nitroanilide. This product is treated with 32% hydrogen bromide in acetic acid at room temperature for one hour, followed by evaporation in vacuo and precipitation with anhydrous ether to provide phenoxyacetyl-L-piepcolyl-L-lysyl-p-nitroanilide hydrobromide.

EXAMPLE X

Following the procedure in Example V, replacing L-arginyl-p-nitroanilide dihydrochloride with $N^\Delta$-benzyloxycarbonyl-L-ornithyl-p-nitroanilide hydrochloride and replacing 0.22 g of phenoxyacetyl-L-proline with 0.23 g of phenoxyacetyl-L-pipecolic acid provides upon purification phenoxyacetyl-L-pipecolyl-$N^\Delta$-benzyloxycarbonyl-L-ornithyl-p-nitroanilide which is then treated with 32% hydrobromide as described in Example VI, providing phenoxyacetyl-L-piepcolyl-L-ornithyl-p-nitroanilide hydrobromide.

EXAMPLE XI

Following the procedure in Example V, replacing phenoxyacetyl-L-proline with phenoxyacetyl-L-azetidinecarboxylic acid provides upon purification phenoxyacetyl-L-azetidinecarbonyl-L-arginyl-p-nitroanilide hydrochloride.

EXAMPLE XII

Following the procedure in Example V, replacing L-arginyl-p-nitroanilide dihydrochloride with $N^\epsilon$-benzyloxycarbonyl-L-lysyl-p-nitroanilide hydrochloride and replacing phenoxyacetyl-L-proline with phenoxyacetyl-azetidine carboxylic acid provides upon purification phenoxyacetyl-L-azetidinecarbonyl-$N^\epsilon$-benzyloxycarbonyl-L-lysyl-p-nitroanilide. This product is treated with 32% hydrogen bromide as described in Example VI providing phenoxyacetyl-L-azetidine-L-lysyl-p-nitroanilide hydrobromide.

EXAMPLE XIII

Following the procedure in Example V, replacing L-arginyl-p-nitroanilide dihydrochloride with $N^\Delta$-benzyloxycarbonyl-L-ornithyl-p-nitroanilide-hydrogen chloride and replacing phenoxyacetyl-L-proline with phenoxyacetyl-L-azetidinecarbonyl-L-ornithyl-p-nitroanilide provides upon purification phenoxyacetyl-L-azetidinecarbonyl-L-ornithyl-p-nitroanilide. This product is treated with 32% hydrogen bromide as described in Example VI, providing phenoxyacetyl-L-azetidinecarbonyl-L-ornithyl-p-nitroanilide hydrobromide.

EXAMPLE XIV $N^\alpha$-benzyloxycarbonyl-$N^w$-(4-methoxybenzenesulfonyl)-L-arginine [as described by Nishimura and Fujino, *Chem. Pharm. Bull.*, 24, (1976)1568-75] is converted to its p-nitroanilide and them hydrolyzed by hydrogen bromide as described by Nishi, et al., *Bull. Chem. Soc. Japan*, 43, (1970)2901-02. The resulting hydrobromide is made basic with one equivalent of triethylamine, and then coupled with t-butoxycarbonyl-L-proline, using the dicyclohexylcarbodiimide in a dimethylformamide (DMF) peptide coupling method [U.S. Pat. No. 3,884,896]. This procedure yields N-t-butoxycarbonyl-L-prolyl-$N^w$-(4-methoxybenzenesulfonyl)-L-arginyl-p-nitroanilide.

EXAMPLE XV

A mixture of 0.65g N-t-butoxylcarbonyl-L-prolyl-$N^w$-(4-methoxybenzenesulfonyl)-L-arginine-p-nitroanilide and 10 ml of 4 M hydrogen chloride in anhydrous dioxane is stirred at room temperature for 25 minutes. The solvent is evaporated in vacuo, and the residue is washed with anhydrous ether to remove excess hydrogen chloride. The product, L-prolyl-$N^w$-(4-methoxybenzenesulfonyl)-L-arginine-p-nitroanilide hydrochloride, is then mixed with 0.152 g of phenoxyacetic acid, 0.10 g of 1-hydroxy-benzotriazole, 5 ml of anhydrous pyridine and 0.25 g of ethyl-dimethylaminopropylcarbodiimide hydrochloride. This mixture is stirred in an ice bath for 45 minutes and then stirred at room temperature for 16 hours. 8 ml of water is added and the solvent evaporated in vacuo. The resulting product is then washed repeatedly with water, citric acid solution, and again with water. The product is phenoxyacetyl-L-prolyl-$N^w$-(4-methoxybenzenesulfonyl)-L-arginyl-p-nitroanilide.

EXAMPLE XVI 0.36 g of vacuum dried phenoxyacetyl-L-prolyl-(4-methoxybenzenesulfonyl)-L-arginyl-p-nitroanilide is dissolved in 1 ml of methylene chloride and 0.2 ml of anisole at 30° C. The mixture is then cooled to 20° C. 1.8 ml of methanesulfonic acid in 1 ml of methylene chloride is added and stirred for 20 minutes. The mixture is allowed to stand at 20° C. for an additional 15 minutes, after which time the mixture is diluted with 30 ml of anhydrous ether. The precipitated product is separated by decanting and washed with fresh anhydrous ether to remove by-products. This provides the methanesulfonic acid salt of phenoxyacetyl-L-prolyl-L-arginyl-p-nitroanilide.

EXAMPLE XVII

The methanesulfonic acid salt of phenoxyacetyl-L-prolyl-L-arginyl-p-nitroanilide is converted to the acetate salt by dissolving the methanesulfonic acid salt in 20 ml of 20% aqueous acetic acid and filtering the solution through 14 g of basic resin acetate. The resin is rinsed with 10 ml of 10% aqueous acetic acid to provide a clear filtrate. The solvent is evaporated from the filtrate in vacuo to provide a residue, and this residue is purified on a silica gel column. The column is eluted with a solvent mixture composed of isopropanol-acetic acid-water in a ratio of 7:2:1, providing the acetic salt of phenoxyacetyl-L-prolyl-L-arginyl-p-nitroanilide.

What is claimed is:

1. A compound of the formula

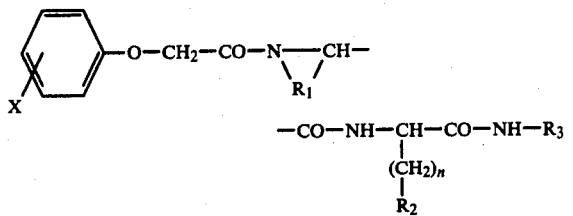

and the biologically acceptable acid addition salts thereof, wherein $R_1$ represents an alkylene having 2–4 carbon atoms; $R_2$ is selected from the group consisting of amino and guanyl; $R_3$ is selected from the group consisting of p-nitrophenyl, methylnitrophenyl, dinitrophenyl, naphthyl and nitronaphthyl; X represents halo or lower alkyl having 1–4 carbon atoms; and n is 3 or 4.

2. A compound of the formula

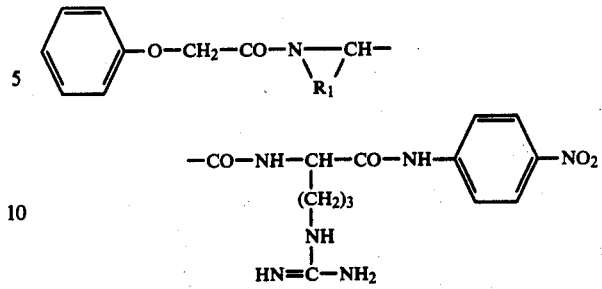

and the biologically acceptable acid addition salts thereof, wherein $R_1$ represents an alkylene having 2–4 carbon atoms.

3. A compound of the formula

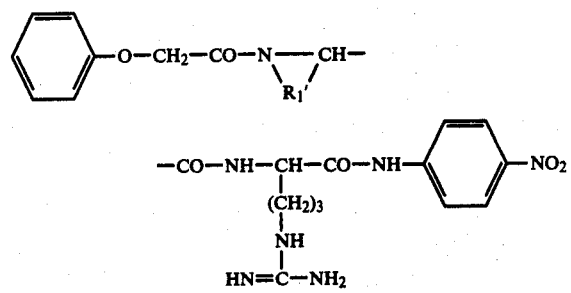

and the biologically acceptable salts thereof, where $R_1'$ represents an alkylene having 3 or 4 carbon atoms.

4. A compound according to claim 3 which is phenoxyacetyl-L-prolyl-L-arginyl-p-nitroanilide.

5. A compound according to claim 3 which is phenoxyacetyl-L-prolyl-L-arginyl-p-nitroanilide hydrochloride.

6. A compound according to claim 3 which is phenoxyacetyl-L-pipecolyl-L-arginyl-p-nitroanilide.

7. A compound according to claim 6 which is phenoxyacetyl-L-pipecolyl-L-arginyl-p-nitroanilide hydrochloride.

* * * * *